United States Patent
Murphy et al.

(10) Patent No.: US 10,196,869 B2
(45) Date of Patent: Feb. 5, 2019

(54) RECYCLE DILUENT FOR WELLBORE FLUID SAMPLING SYSTEM

(71) Applicant: Halliburton Energy Services, Inc., Houston, TX (US)

(72) Inventors: Robert J. Murphy, Kingwood, TX (US); Sandeep D. Kulkarni, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/525,525

(22) PCT Filed: Dec. 23, 2014

(86) PCT No.: PCT/US2014/072196
§ 371 (c)(1),
(2) Date: May 9, 2017

(87) PCT Pub. No.: WO2016/105391
PCT Pub. Date: Jun. 30, 2016

(65) Prior Publication Data
US 2017/0321505 A1    Nov. 9, 2017

(51) Int. Cl.
*E21B 21/01* (2006.01)
*E21B 41/00* (2006.01)
(Continued)

(52) U.S. Cl.
CPC .............. *E21B 21/01* (2013.01); *E21B 41/00* (2013.01); *G01N 1/38* (2013.01); *G01N 15/0227* (2013.01); *G01N 33/2823* (2013.01); *E21B 21/00* (2013.01); *G01N 15/00* (2013.01); *G01N 2015/0053* (2013.01)

(58) Field of Classification Search
CPC .......... E21B 21/01; E21B 41/00; E21B 21/00; E21B 49/08; G01N 1/38; G01N 33/2823
See application file for complete search history.

(56) References Cited

U.S. PATENT DOCUMENTS 5,283,001 A    2/1994   Gregoli et al.
7,402,636 B1   7/2008   Shaffer et al.
(Continued)

OTHER PUBLICATIONS

International Search Report and Written Opinion for Application No. PCT/US2014/072196 dated Sep. 16, 2015.

*Primary Examiner* — Zakiya W Bates
(74) *Attorney, Agent, or Firm* — Tenley Krueger; Tumey L.L.P.

(57) ABSTRACT

A wellbore fluid sampling system may comprise a mixing system coupled to a wellbore sample supply and a recycled diluent supply, a fluid analysis system coupled to the mixing system, and a diluent recycle system coupled to the fluid analysis system and the mixing system, wherein the diluent recycle system comprises an evaporator and a condenser. A method for recycling diluent may comprise combining a wellbore fluid sample with a diluent to form a diluted wellbore fluid sample, analyzing the diluted wellbore fluid sample to determine one or more fluid properties, separating at least a portion of the diluent from the wellbore fluid sample in the diluted wellbore fluid sample, and recycling the separated portion of the diluent for re-use.

19 Claims, 4 Drawing Sheets

(51) Int. Cl.
*G01N 1/38* (2006.01)
*G01N 15/02* (2006.01)
*G01N 33/28* (2006.01)
G01N 15/00 (2006.01)
E21B 21/00 (2006.01)

(56) References Cited

U.S. PATENT DOCUMENTS

2008/0093072 A1   4/2008  Oakley et al.
2009/0126928 A1   5/2009  Sumrall et al.
2010/0319921 A1  12/2010  Eia et al.
2014/0202664 A1   7/2014  Schexnaider et al.
2014/0250987 A1*  9/2014  Canty ..................... G01N 1/38
                                                 73/64.56

* cited by examiner

RECYCLE DILUENT FOR WELLBORE FLUID SAMPLING SYSTEM

BACKGROUND

Provided are systems and methods for diluting wellbore fluid samples for analysis. More particularly, systems and methods may be provided for a real-time analysis of particle size distribution by diluting drilling fluid samples at a well site.

During the drilling of a wellbore into a subterranean formation, a drilling fluid, also referred to as a drilling mud, may be continuously circulated from the surface down to the bottom of the wellbore being drilled and back to the surface again. The drilling fluid serves several functions, one of them being to transport wellbore cuttings up to the surface where they are separated from the drilling fluid. Another function of the drilling fluid is to provide hydrostatic pressure on the walls of the drilled wellbore so as to prevent wellbore collapse and the resulting influx of gas or liquid from the formations being drilled. For several reasons, it may be important to precisely know the characteristics and chemical composition of the drilling fluid.

Determining particle size distribution in drilling operations is beneficial to an efficient drilling operation. Particle size distribution determination may allow operators of a drilling operation to estimate the filter cake properties downhole, characterize drill cuttings found in the drilling fluid, and/or determine the types of filters need to properly screen drilling fluid coming from downhole. For example, particle sizes may indicate filter cake properties such as filter cake thickness, toughness, slickness and permeability. Large particles may cause drilling problems such as stuck pipe and low flow of drilling fluid and smaller particles may not isolate formations from drilling fluids. A preferred particle size distribution, for a specific drilling operation, may need to be checked regularly, allowing a drilling operator to monitor to particle size within drilling fluid.

The frequency of analysis required in drilling operations may make the current methods unduly burdensome. Frequently, drilling fluid samples need to be diluted before analysis. Diluent may need to be constantly transported to the drilling site and mixed with the drilling fluid sample with the waste mixture of the drilling fluid sample and diluent needing to be transported to a disposal area. This may inhibit the ability for an analysis system to function for long periods of time and create large amounts of diluent or waste. Furthermore, the diluent, as well as waste mixture of diluent and drilling fluid sample, may need to be stored on site. This may take up large amounts of space around drilling operations, hindering operation.

BRIEF DESCRIPTION OF THE DRAWINGS

These drawings illustrate certain aspects of some examples of the present invention, and should not be used to limit or define the invention.

DETAILED DESCRIPTION

Figure 1:
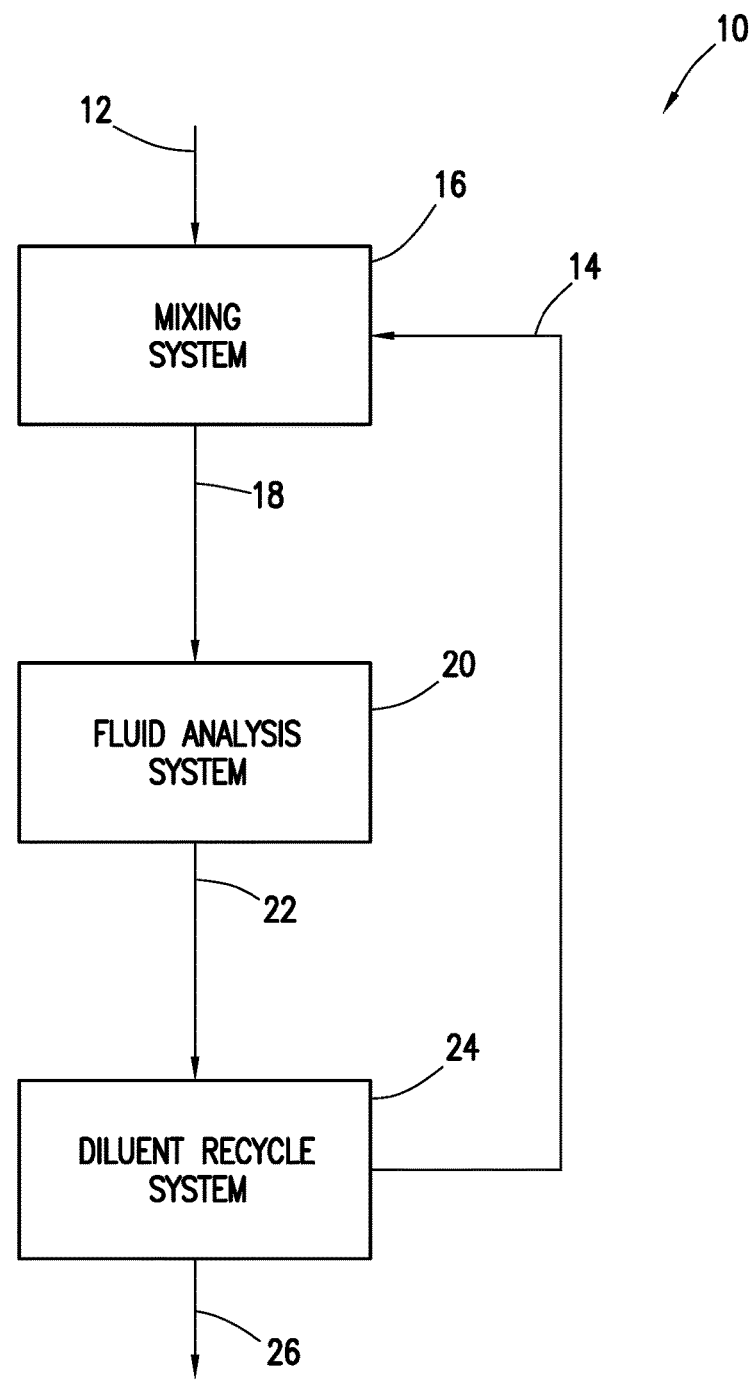
FIG. 1 illustrates an example block diagram using recyclable diluent.

Provided are systems and methods for diluting wellbore fluid samples for analysis. More particularly, systems and methods may be provided for a real-time analysis of particle size distribution by diluting drilling fluid samples at a well site.

As disclosed below, methods and systems are provided to reduce waste and/or amount of space needed for wellbore fluid sample analysis. When analyzing wellbore fluids, wellbore fluid samples may be frequently diluted before analysis. This may be problematic for situations in the field because of the requirements to furnish enough diluent and further the need for disposal of the diluent after use. The frequency of analysis required in drilling operations may make the current methods unduly burdensome. Diluent may need to be constantly transported to a well site and diluted wellbore fluid samples mud may need to be transported to a disposal area after analysis. Advantageously, the systems and methods disclosed herein may allow for the re-use of diluent, allowing the supply and disposal problems to be greatly mitigated. This may make it possible to perform fluid analysis techniques for longer periods of time without large amounts of diluent or waste.

Commonly, wellbore fluid analysis systems may be housed in compact enclosures to protect them in the drilling rig environment. Because of the potential flammable vapors escaping from a wellbore during abnormal drilling situations, analysis system enclosures are frequently pressured slightly with air or nitrogen so that flammable gases cannot enter the enclosure from the environment where the internal electrical components may possibly ignite them. A safety system may insure that the enclosure is pressurized and purged of ambient gasses before the electrical systems in the enclosure are energized. The initial purge of the enclosure may take about fifteen to forty five minutes or more and must be repeated every time the enclosure is opened for maintenance. It is highly desirable that any expendable fluid or material need for the wellbore fluid analysis last for two weeks or more to minimize analysis system unavailability due to purging. For these reasons, it is desirable that any consumables, such as diluents, needed for wellbore fluid analysis should be contained in the enclosure and recycled within the enclosure.

A wellbore fluid sampling system may be provided. The wellbore fluid sampling system may comprise a mixing system coupled to a wellbore sample supply and a recycled diluent supply, a fluid analysis system coupled to the mixing system, and a diluent recycle system coupled to the fluid analysis system and the mixing system, wherein the diluent recycle system comprises an evaporator and a condenser. The fluid analysis system may comprise at least one analysis system selected from the group consisting of an optical measuring system, an imaging measuring system, a laser measuring system, and ultrasound measuring system a pH measuring system, and a titration system. The fluid analysis system may further comprise a digital camera and an optical flow cell, wherein the digital camera may be positioned to image fluids passing though the optical flow cell. The recycled diluent supply of the wellbore fluid sampling system may comprise at least one diluent selected from the group consisting of isopropyl alcohol, diethyl ether, butane, 1,1,1,2-tetrafluoreoethane, 2,3,3,3-tetrafluoropropene, hexane, xylene, and propylene glycol normal propyl ether.

The wellbore sample supply of the wellbore fluid sampling system may comprise a drilling fluid sample. The diluent recycle system further may comprise a compressor, wherein the compressor may be positioned to receive separated vapor from the evaporator. The evaporator of the wellbore fluid sampling system may be a wiped-film evaporator. The evaporator may be configured to receive compressed gas comprising diluent from the compressor for recovery of heat. The diluent recycle system further may comprise a diluent supply vessel for receiving condensed diluent from the condenser. The mixing system and the fluid analysis system may be combined.

A method for recycling diluent may be provided. The method may comprise combining a wellbore fluid sample with a diluent to form a diluted wellbore fluid sample, analyzing the diluted wellbore fluid sample to determine one or more fluid properties, separating at least a portion of the diluent from the wellbore fluid sample in the diluted wellbore fluid sample, and recycling the separated portion of the diluent for re-use. The wellbore fluid sample used in the recycling diluent method may be a drilling fluid. The wellbore fluid sample may be a sample of a drilling fluid comprising an oil phase and a water phase, wherein the diluent may be miscible in the oil phase and the water phase of the drilling fluid. The diluent may comprise at least one diluent selected from the group consisting of isopropyl alcohol, diethyl ether, butane, 1,1,1,2-tetrafluoreoethane, 2,3,3,3-tetrafluoropropene, hexane, xylene, and propylene glycol normal propyl ether. The step of analyzing the diluted wellbore fluid sample may comprise imaging the diluted wellbore fluid sample. The step of analyzing the diluted wellbore fluid further may comprise determining a particle size distribution of the diluted wellbore fluid sample. The step of separating the diluent from the wellbore fluid may comprise evaporating the portion of the diluent from the wellbore fluid sample. The step of recycling the recycling diluent further may comprise compressing the separated portion of the diluent and recovering heat generated by the step of compressing for evaporation of the portion of the diluent from the wellbore fluid sample. The method of recycling diluent further may comprise condensing the separated vapor at a temperature of about −40° F. to about 110° F. to form a condensed diluent. The method of recycling diluent further may comprise filtering the condensed diluent.

Referring now to FIG. 1, a block flow diagram is shown generally depicting a fluid sampling system 10 for sample analysis with diluent recycling. As illustrated, a wellbore fluid sample from sample supply 12 comprising a wellbore fluid sample may be combined with a recycled diluent supply 14 comprising diluent in a mixing system 16. A diluted fluid supply 18 comprising the wellbore fluid sample and diluent may be fed to a fluid analysis system 20 for sample analysis. After sample analysis, a diluted fluid effluent 22 comprising the wellbore fluid sample and diluent may be fed to a diluent recycle system 24 for recovery of the diluent. In the diluent recycle system 24, the diluent may be separated from the wellbore fluid sample in the diluted fluid effluent 22 to provide recycled diluent supply 14 for recycle and re-use, as well as a recovered wellbore fluid sample 26, as illustrated on FIG. 1.

The wellbore fluid sample may be a sample of any wellbore fluid in which analysis, for example, at a well site, may be desired. Without limitation, the wellbore fluid may include drilling fluids, fracturing fluids, lost circulation fluids, displacement fluids, drill-in fluids, and any other type of treatment fluid in which dilution for analysis may be needed. The drilling fluid may include either an oil-based drilling fluid or a water-based drilling fluid. The wellbore fluid sample may comprise solids. The solids may be any type of solids found in a wellbore or introduced into a wellbore fluid. Without limitation, examples of solids may include pieces of the formation, drill cuttings, and additives introduced to a wellbore fluid, e.g., lost circulation materials, proppants, etc. The solids may be of any of a variety of sizes and shapes. The wellbore fluid sample may be analyzed as described herein to determine one or more fluid properties. For example, the wellbore fluid may be analyzed to determine particle size distribution.

The diluent may include any of a variety of diluents that may be used to dilute a wellbore fluid sample for analysis. In examples, optical methods may be used for fluid analysis to "see" the particles in the wellbore fluid sample. Optical methods may require the wellbore fluid sample to be greatly diluted. In many applications, the ratio of the wellbore fluid sample to the diluent may need to be 2:1, 3:1, 10:1, 100:1, 1000:1, or greater. Diluting the wellbore fluid sample separates particles and increase optical transparency.

Currently, many different types of diluents may be used to dilute wellbore fluid samples, such as samples of oil-based and water-based drilling fluid. In some instances, the base fluid of the wellbore fluid sample may be used as the diluent, but this type of diluent may be difficult to separate. In addition, the diluted wellbore fluid sample may not have the optical or physical properties needed for the analysis. Therefore, a different diluent than the base fluid may selected. For such cases, to ensure an enclosed stand-alone operation and minimization of storage and waste disposal, recycling of diluent may be necessary. The recycling of diluent may be achieved by separation from the fluid using a distillation process. The distillation may be carried out by either two principal methods. The first method is where there is no reflux, in other words, the diluted wellbore fluid sample may be boiled and vapor may be condensed without allowing any liquid returning to the still. The second method is based on reflux, in other words, diverting a part of the condensate back to the still where it may come in contact with vapor going to condenser. Either of these two methods may be conducted as batch or continuous process. The method without reflux, if carried as continuous process is called flash distillation while there may also a process of batch distillation without reflux. To the contrary, the method with reflux, if carried as continuous process is called rectification (e.g. sieve-tray distillation column) while there may also a process of batch distillation with reflux. Vacuum distillation or steam distillation may be used for separating components with relatively high boiling points. Additionally, azeotropic distillation may be used if the components of the solution form azeotropic mixture where the composition of the components in the liquid is same as that in vapor.

A recyclable diluent may have one or more of the following properties: ease of separation (e.g., boiling points), solubility characteristics, and/or breaking emulsion characteristics. However, many diluents may not be suitable for samples of both types of drilling fluids. This may lead to two or more diluents being transported to a drill site, incurring more waste for disposal. An ideal diluent may work for both fluids. It is not unusual during drilling operations to switch between water based and oil based wellbore treatment fluids. A single diluent for all fluids may greatly simplify the design and operation. However, it may be necessary to modify the operation parameters depending on whether or not a water based or oil based wellbore treatment fluid is used. Operating parameter that may change are temperature and pressure. For the separation techniques disclosed herein, it may be desirable for the boiling point of the diluent to be substantially lower than the standard boiling point of anything in the wellbore fluid sample. For safety and environmental reasons, most wellbore fluids have standard boiling points higher than about 100° C. at atmospheric pressure and normal surface operating temperatures. Volatile diluents with boiling points lower than 100° C. may be more easily separated from the wellbore fluids by distillation processes. At a given evaporator temperature, the wider the gap between the vapor pressure of the wellbore fluid components and the diluent, the more discriminating the distillation process will be. Diluents that are vapors at ambient conditions, but liquids at pressures less than about 14 bar may be used. These diluents may be easily separated from the diluted wellbore fluid sample with minimal temperature increase in the evaporator. However, the diluent vapor from the evaporator may have to be compressed and cooled to re-liquefy it for reuse. In most cases, it may be desirable to use diluents with critical temperatures below the maximum ambient temperature experienced on a drilling rig. For example, the following diluents have a range of boiling points, allowing for different diluents to be used in different environments. The diluent propylene glycol has a boiling point of 188° C., isopropyl alcohol has a boiling point of 82.6° C., diethyl ether has a boiling point of 34.6° C., xylene has a boiling point of 140° C., hexane has a boiling point of 69° C., butane has a boiling point of 1° C., 1,1,1,2-tetrafluoroethane has a boiling point of −26° C., and 2,3,3,3-tetrafluoropropene has a boiling point of −30° C. In addition, the use of a non-flammable diluent under normal conditions may reduce the risk of fires and explosions. Volatile diluents may have low global warming potential and be relatively non-toxic.

The chosen diluent for the method may further depend on a desired operating condition and fluid analysis technique used. Based on solubility characteristics, the diluent may be categorized into three types, for example, water soluble diluents, oil soluble diluents, or mutual solvents. Examples of suitable water soluble diluents may comprise propylene glycol, isopropyl alcohol, and diethyl ether. Examples of suitable oil soluble diluents may comprise xylene, hexane, butane, 1,1,1,2-tetrafluoroethane (Refrigerant 134a), and 2,3,3,3-tetrafluoropropene (Refrigerant HFO-1234yf). Examples of suitable mutual solvents may comprise glycol ethers such as propylene glycol n-butyl ether, and ethylene glycol monoethyl ether. Combinations of diluents may also be used.

Many wellbore fluids may be emulsions of water or brine in oil which are stabilized with emulsifiers. Large dilution ratios may destabilize the emulsion by diluting the emulsifier to the point where it is no longer effective. In that case, the water phase may tend to coalesce to form larger droplets which may confuse some particle analysis techniques. The drops may form optically distorting layers on optical windows or appear as large particles. In addition to coalescing, the water phase may also wet the particles in the wellbore fluid, causing them to conglomerate. Conglomerated water-wet particles may not be differentiated and be counted as one large particle. For fluid analysis techniques using optical sensors that may require optical clarity for particle size measurement, it may be desirable to use a diluent that is miscible in both the water and oil phase of the wellbore fluid sample, such as a drilling fluid, should both these phases be present. Otherwise, the water or oil may show up as droplets that may be counted in the particle size distribution and the previously mentioned problems may occur. In still other cases, it may be desirable to add a small volume of suitable emulsifier while diluting to compensate for the dilution and keep the emulsion stable.

Alternatively, the coalescence of the water phase may be desirable. For example when the salinity or pH of the water phase is being measured it may be desirable to "break" the emulsion and separate the water phase so that various analytical probes or titrations can be used on that phase alone. An example of a suitable diluent for this purpose may be n-propoxy propanol (PnP).

Mixing system 16 may use any suitable mixing technique for mixing of the wellbore fluid sample and the diluent in a designated ratio. For example, the ratio of the wellbore fluid sample to the diluent may need to be 2:1, 3:1, 10:1, 100:1, 1000:1, or greater. The ratio may be determined using feedback from the accurately controlled fluid analysis system 20. In order to calculate the particle size volume percent, the dilution ratio may need to be accurately controlled. For example, if particles are being counted and measured, the particle concentration may be a feedback to the mixing system 16 to optimize dilution. While not illustrated, in examples, surfactants, de-emulsifiers, or other suitable additives may also be combined with the wellbore fluid sample and diluent in the mixing system 16. The mixing system 16 may use any of a variety of different mixing equipment, such as static or dynamic mixers. One example of suitable mixing equipment may comprise a vessel with a paddle wherein the paddle may be used to mixing the wellbore fluid sample with the diluent. Pumps or other delivery equipment may be used for delivery of the wellbore fluid sample and the diluent to the mixing system 16.

In the fluid analysis system 20, the wellbore fluid sample may be analyzed to determine one or more properties thereof. A variety of different techniques may be used for fluid analysis. Without limitation, fluid analysis techniques may include optical measuring systems, imaging measuring systems, laser measuring systems, ultrasound measuring systems, pH measuring systems, and titration systems, among others. Combinations of fluid analysis techniques may also be used. The fluid analysis system 20 may be used to determine a particle size distribution in the wellbore fluid sample. Optical methods may be used for determining particle size distribution. The particle size distribution may be further reviewed by a drilling operator.

The diluent recycle system 24 may be used for recovery of the diluent. As illustrated, the diluent recycle system 24 may separate the diluted fluid effluent 22 into a recovered wellbore fluid sample 26 and a recycled diluent supply 14. Separation may be accomplished using any of a variety of different techniques, including distillation, wiped film evaporation, vapor-compression evaporation, and flash evaporation, among others. Specific distillation techniques that may be used for this separation have been discussed previously. The recycled diluent supply 14 which is separated may be sent back to mixing system 16 for re-use, allowing for the method to be repeated. After the recycled diluent supply 14 has been removed, recovered wellbore fluid sample 26 is restored to its near original state. Although 100% recovery of recovered wellbore fluid sample 26 may not be possible, nearly unaltered, recovered wellbore fluid sample 26 may be returned to the main wellbore fluid stream. Current methods do not separate the wellbore fluid sample and diluent after analysis. Instead, the diluted effluent 22 comprising the wellbore fluid sample and diluent are typically stored on the well site to be removed and disposed at a separate location. Current methods may lead to large amounts of waste and large areas around the well site being used to house the diluted fluid effluent 22.

Figure 2:
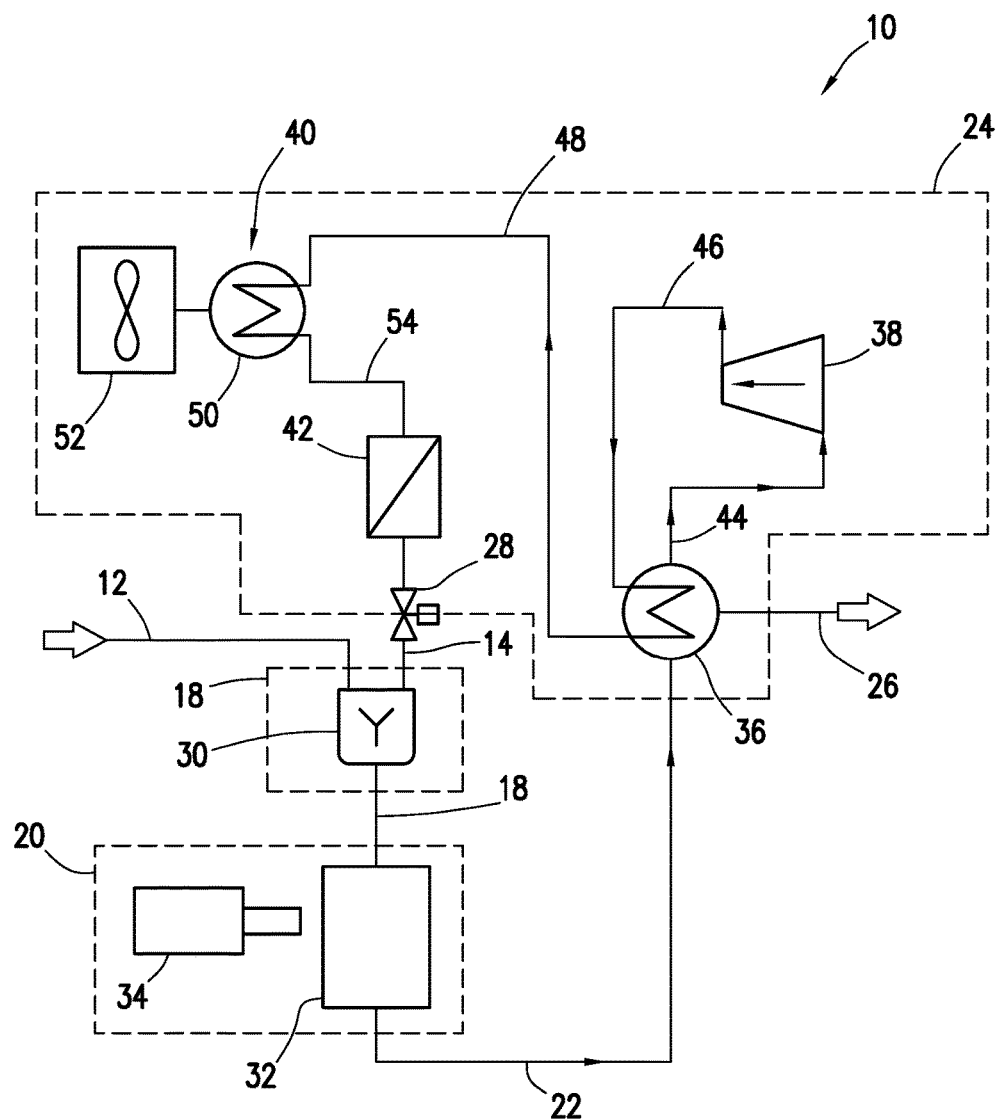
FIG. 2 illustrates an example fluid sampling system using a diluent to analyze drilling fluid from a drilling operation.

Referring now to FIG. 2, an example of the fluid sampling system 10 is shown in more detail. As illustrated, the fluid sampling system 10 may comprise mixing system 16, fluid analysis system 20, and diluent recycle system 24. A sample supply 12 may pull samples of a wellbore fluid and flow the wellbore fluid samples to the mixing system 16. A recycled diluent supply 14 may flow diluent to the mixing system 16. Control valve 28 may be disposed in the recycled diluent supply 14 to control flow of the diluent to the mixing system 16. Mixing system 16 may comprise mixer 30. Mixer 30 may be a static mixer, dynamic mixer, of other suitable mixer for combining the wellbore fluid sample and the diluent. One example of a suitable mixer 30 may comprise a vessel with a paddle wherein the paddle may be used to mixing the wellbore fluid sample with the diluent.

Figure 3:
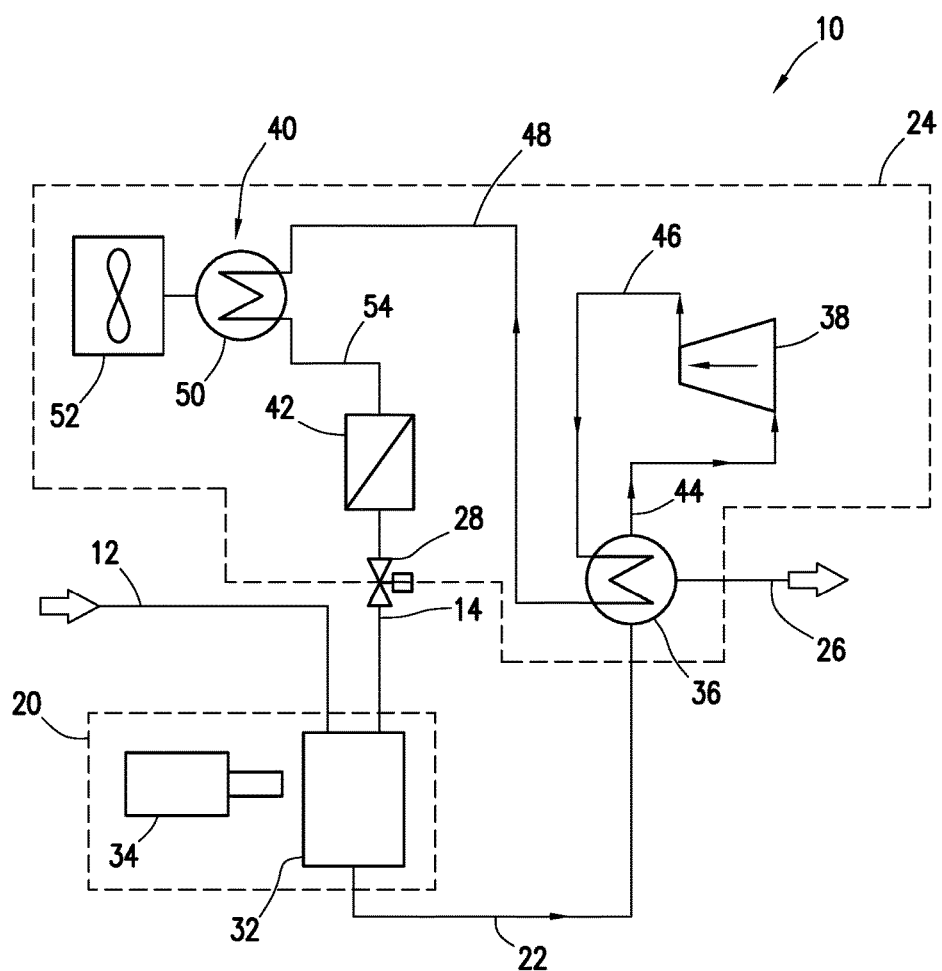
FIG. 3 illustrates another example fluid sampling system using a diluent to analyze drilling fluid from a drilling operation.

There may be no need for a separate mixing system 16 to combine sample supply 12 and diluent supply 14 before transfer to fluid analysis system 20. As illustrated in FIG. 3, sample supply 12 and diluent supply 14 may be combined and mixed within fluid analysis system 20. Sample supply 12 and diluent supply 14 may be combined and mixed within a vessel or volume inside fluid analysis system 20, such as optical flow cell 32.

Referring again to FIG. 2, a diluted fluid supply 18 comprising the wellbore fluid sample and diluent from the mixing system 16 may be fed to the fluid analysis system 20. As previously mentioned, the fluid analysis system 20 may include any of a variety of different systems for analysis of the wellbore fluid sample. As illustrated, the fluid analysis system 20 may comprise an optical flow cell 32 into which the diluted fluid supply 18 may be fed. Digital camera 34 may be positioned to image the diluted fluid supply 18 as it passes through the optical flow cell 32 and allow determination of the particle size distribution in the diluted fluid supply 18.

Diluted fluid effluent 22 comprising the wellbore fluid sample and diluent may flow from the fluid analysis system 20 to the diluent recycle system 24. A set of connecting pipes or hoses may be used to pass the diluted fluid effluent 22 from the fluid analysis system 20 to the diluent recycle system 24. As illustrated, the diluent recycle system 24 may comprise an evaporator 36, a compressor 38, a condenser 40, and a diluent supply vessel 42.

In the diluent recycle system 24, the diluted fluid effluent 22 may be passed to the evaporator 36. In the evaporator 36, the diluent may be evaporated from the wellbore fluid sample by manipulating temperature and/or pressure in the evaporator 36. For example, the diluted fluid effluent 22 may be heated in the evaporator 36 to vaporize the diluent. In combination with heating or as a separate evaporation process, the pressure of the diluted fluid effluent 22 may be reduced in the evaporator 36 for vaporization of the diluent. While not illustrated, a valve may be located at the entry of the evaporator 36 so that the diluted fluid effluent 22 undergoes flash evaporation within the evaporator 36. The diluent may have a vapor pressure many times higher than water at conditions within evaporator 36. This may produce a distillation process. Based upon the dwell time in evaporator 36, multiple stages of evaporation may be required to recover all of the diluent. The evaporation may transform the diluted fluid effluent 22 into separated vapor 44 and recovered wellbore fluid sample 26 both of which may be removed from the evaporator 36. The separated vapor 44 may comprise separation portion the diluent and potentially some other species from the wellbore fluid sample. Separate of about ninety percent, about ninety nine percent, or higher is expected. The recovered wellbore fluid sample 26 may be disposed of or re-used, for example, by return to a mud pit or other wellbore fluid reservoir.

In general, the evaporator 36 may comprise any suitable device or combination of devices suitable for evaporative separation of the diluent (e.g., separated gas 38) from the wellbore fluid sample (e.g., recovered wellbore fluid sample 26). By way of example, the evaporator 36 may comprise a wiped-film evaporator. Wiped-film evaporators may be desirable, for example, to prevent solids build up on the heat transfer surfaces during the evaporation process where the wellbore fluid sample may have high solids concentrations and gelling properties. Other suitable examples of an evaporator 36 may include plate type evaporators and force circulation evaporators After removal from the evaporator 36, the separated vapor 44 comprising diluent may flow to compressor 38. Depending on the type of diluent used, the compressor 38 may be used to lower the pressure in the evaporator 36. In the compressor 38, the separated vapor 44 may be compressed to a higher pressure resulting in a higher temperature as well. In examples, it may be necessary to raise the pressure of the separated vapor 44 with compressor 32 considerably above atmospheric, allowing the diluent to condense at the required temperature. In general, the compressor 38 may comprise any suitable device or combination of devices suitable for compression of the separated vapor 44. By way of example, the compressor 38 may comprise any type of compressor, such as a rotary screw, turbo, scroll, or reciprocating compressor.

The heat generated by compressing the separated vapor 44 may be recovered by passing the compressed vapor 46 through the evaporator 36 such that the compressed vapor 46 may be used to heat the diluted fluid effluent 22. In the evaporator 36, thermal energy from the compressed vapor 46 may be transferred to the diluted fluid effluent 22. However additional heat may be required. Additional heat may be supplied by electric resistance heaters or Peltier heaters. Peltier heat pumps may remove heat from condenser 40 to evaporator 36. Cooled, compressed vapor 46 may be passed from the evaporator 36 to the condenser 40. In condenser 40, the cooled, compressed vapor 46 may be cooled and condensed into a liquid. Condenser 40 may operate, for example, at a temperature at about, or a little above, ambient. By way of example, condenser 40 may operate by cooling the cooled, compressed vapor 46 to a temperature from about 50° F. to about 100° F. Within the condenser 34 relatively pure diluent may be recovered as a liquid for re-use. By way of example, the liquid recovered in the condenser 34 may comprise diluent in an amount of about 90%, about 95%, or even greater diluent by weight. The condensed diluent may comprise the separated portion of the diluent that was separated in the evaporator 36. In general, the condenser 40 may comprise any suitable device or combination of devices suitable for cooling and condensing of the cooled, compressed vapor 46. By way of example, the condenser 40 may comprise fins and tubes, such as air coils or a shell and tube. As illustrated, the condenser 40 may comprise a heat exchanger 50 and a fan 52 for blowing air across the heat exchanger 50.

Condensed diluent 54 from the condenser 40 may be recovered in a diluent supply vessel 42 for re-use, as illustrated in FIG. 2. Diluent supply vessel 42 may further comprise filters, which may further filter the condensed diluent 54 before re-use. It may be desirable to remove impurities, such as water or other components, from the condensed diluent 54, for example, by filtration or drying, to ensure desired purity and the properties of the condensed diluent 54. Recycled diluent 14 may be provided from the diluent supply vessel 42 to the mixing system 16 for re-used in the fluid sampling system 10.

Figure 4:
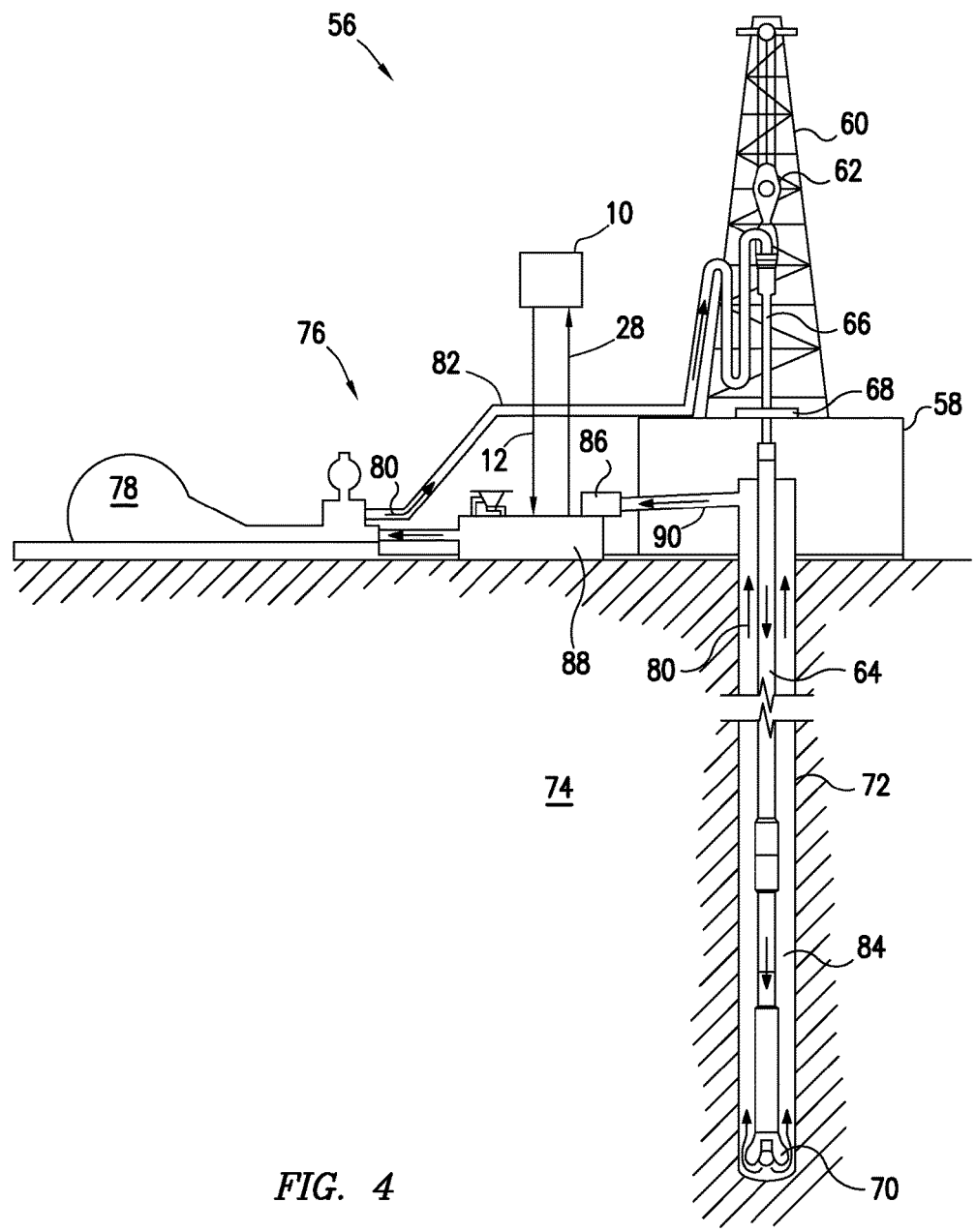
FIG. 4 illustrates an example drilling fluid system using a fluid sampling system.

Referring now to FIG. 4, the disclosed fluid sampling system 10 may be used with an exemplary drilling system 56. It should be noted that while FIG. 4 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 56 may include a drilling platform 58 that supports a derrick 60 having a traveling block 62 for raising and lowering a drill string 64. The drill string 64 may include, but is not limited to, drill pipe and coiled tubing, as generally known to those skilled in the art. A kelly 66 may support the drill string 64 as it may be lowered through a rotary table 112. A drill bit 70 may be attached to the distal end of the drill string 64 and may be driven either by a downhole motor and/or via rotation of the drill string 64 from the well surface. Without limitation, the drill bit 70 may include, roller cone bits, PDC bits, natural diamond bits, any hole openers, reamers, coring bits, and the like. As the drill bit 70 rotates, it may create a borehole 72 that penetrates various subterranean formations 74.

The drilling system 56 may further include a fluid handling system 76, which may include a pump 78, one or more fluid processing units 86, and a drilling fluid reservoir 88 (e.g., a vessel, mud pit, etc.). The pump 78 representatively includes any conduits, pipelines, trucks, tubulars, and/or pipes used to fluidically convey the drilling fluid 80 downhole, any pumps, compressors, or motors (e.g., topside or downhole) used to drive the drilling fluid 80 into motion, any valves or related joints used to regulate the pressure or flow rate of the drilling fluid 80, and any sensors (e.g., pressure, temperature, flow rate, etc.), gauges, and/or combinations thereof, and the like. The fluid processing unit(s) 86 may include, but are not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, any fluid reclamation equipment. The fluid processing unit(s) 86 may further include one or more sensors, gauges, pumps, compressors, and the like used store, monitor, regulate, and/or recondition the drilling fluid and various additives thereto.

The pump 78 (e.g., a mud pump) may circulate drilling fluid 80 through a feed pipe 82 and to the kelly 66, which may convey the drilling fluid 80 downhole through the interior of the drill string 64 and through one or more orifices in the drill bit 70. The drilling fluid 80 may then be circulated back to the surface via an annulus 84 defined between the drill string 64 and the walls of the borehole 72. At the surface, the recirculated or spend drilling fluid 80 may be conveyed to the fluid processing unit(s) 86 via an interconnecting flow line 90. After passing through the fluid processing unit(s) 86, a "cleaned" drilling fluid 80 may be deposited into a nearby drilling fluid reservoir 88. While illustrated as being arranged at the outlet of the wellbore 72 via the annulus 84, those skilled in the art will readily appreciate that the fluid processing unit(s) 86 may be arranged at any other location in the drilling system 56 to facilitate its proper function, without departing from the scope of the scope of the disclosure.

Referring still to FIG. 4, the drilling system 56 may further include a fluid sampling system 10, which may be disposed on a skid supported on the platform 58. The fluid sampling system 10 may be in fluid communication with the fluid handling system 76. The fluid sampling system 10 may, for example, continuously or intermittently sampling drilling fluid 80 from the fluid handling system 76 to analyze the drilling fluid 80 returning from annulus 84. As illustrated, wellbore fluid samples of the drilling fluid 80 may be taken from the drilling fluid reservoir 88 via a fluid supply 28 and a recovered fluid sample 12 may be returned to the drilling fluid reservoir 88. Alternatively, the wellbore fluid samples of the drilling fluid 80 may be taken from the fluid processing units 86 or from before the fluid processing units 86, for example, if unprocessed fluid samples are desired for analysis.

Therefore, the present invention is well adapted to attain the ends and advantages mentioned as well as those that are inherent therein. The particular examples disclosed above are illustrative only, as the present invention may be modified and practiced in different but equivalent manners apparent to those skilled in the art having the benefit of the teachings herein. Although individual examples are discussed, the invention covers all combinations of all those examples. Furthermore, no limitations are intended to the details of construction or design herein shown, other than as described in the claims below. It is therefore evident that the particular illustrative examples disclosed above may be altered or modified and all such variations are considered within the scope and spirit of the present invention. All numbers and ranges disclosed above may vary by some amount. Whenever a numerical range with a lower limit and an upper limit is disclosed, any number and any included range falling within the range are specifically disclosed. Moreover, the indefinite articles "a" or "an," as used in the claims, are defined herein to mean one or more than one of the element that it introduces. Also, the terms in the claims have their plain, ordinary meaning unless otherwise explicitly and clearly defined by the patentee. If there is any conflict in the usages of a word or term in this specification and one or more patent or other documents that may be incorporated herein by reference, the definitions that are consistent with this specification should be adopted for the purposes of understanding this invention.

What is claimed is:

1. A wellbore fluid sampling system comprising:
    a mixing system coupled to a wellbore sample supply and a recycled diluent supply;
    a fluid analysis system coupled to the mixing system; and
    a diluent recycle system coupled to the fluid analysis system and the mixing system,
    wherein the diluent recycle system comprises an evaporator and a condenser and wherein the wellbore sample supply comprises a fluid returning from an annulus in the wellbore.

2. A system according to claim 1, wherein the fluid analysis system comprises at least one analysis system selected from the group consisting of an optical measuring system, an imaging measuring system, a laser measuring system, an ultrasound measuring system, a pH measuring system, and a titration system.

3. A system according to claim 2, wherein the fluid analysis system comprises a digital camera and an optical flow cell, wherein the digital camera is positioned to image fluids passing through the optical flow cell.

4. A system according to claim 1, wherein the recycled diluent supply comprises at least one diluent selected from the group consisting of propylene glycol, isopropyl alcohol, diethyl ether, glycol ether, butane, 1,1,1,2-tetrafluoroethane, 2,3,3,3-tetrafluoropropene, hexane, xylene, propylene glycol normal propyl ether, and n-propoxy propanol.

5. A system according to claim 1, wherein the wellbore sample supply comprises a drilling fluid sample.

6. A system according to claim 1, wherein the diluent recycle system further comprises a compressor, and wherein the compressor is positioned to receive separated vapor from the evaporator.

7. A system according to claim 1, wherein the evaporator is a wiped-film evaporator.

8. A system according to claim 6 wherein the evaporator is configured to receive compressed gas comprising diluent from the compressor for recovery of heat.

9. A system according to claim 1, wherein the mixing system and fluid analysis system are combined.

10. A system according to claim 1, wherein the system is in fluid communication with a fluid handling system of a drilling system.

11. A method for recycling diluent, comprising:
    obtaining a wellbore fluid sample from a wellbore fluid returning from an annulus of a wellbore;
    combining the wellbore fluid sample with a diluent to form a diluted wellbore fluid sample;
    analyzing the diluted wellbore fluid sample to determine one or more fluid properties;
    separating at least a portion of the diluent from the wellbore fluid sample in the diluted wellbore fluid sample, wherein the step of separating comprises evaporating the portion of the diluent from the wellbore fluid sample; and
    recycling the separated portion of the diluent for re-use.

12. A method according to claim 11, wherein the wellbore fluid sample is a drilling fluid.

13. A method according to claim 12, wherein the wellbore fluid sample is a sample of a drilling fluid comprising an oil phase and a water phase, wherein the diluent is miscible in the oil phase and the water phase of the drilling fluid.

14. A method according to claim 11, wherein the diluent comprises at least one diluent selected from the group consisting of propylene glycol, isopropyl alcohol, diethyl ether, glycol ether, butane, 1,1,1,2-tetrafluoroethane, 2,3,3,3-tetrafluoropropene, hexane, xylene, propylene glycol, normal propyl ether, and n-propoxy propanol.

15. A method according to claim 11, wherein the step of analyzing comprises imaging the diluted wellbore fluid sample.

16. A method for recycling diluent, comprising:
    obtaining a wellbore fluid sample from a wellbore fluid returning from an annulus of a wellbore;
    combining the wellbore fluid sample with a diluent to form a diluted wellbore fluid sample;
    analyzing the diluted wellbore fluid sample to determine one or more fluid properties;
    separating at least a portion of the diluent from the wellbore fluid sample in the diluted wellbore fluid sample; and
    recycling the separated portion of the diluent for re-use,
    wherein the step of analyzing comprises imaging the diluted wellbore fluid sample and determining a particle size distribution of the diluted wellbore fluid sample.

17. A method for recycling diluent, comprising:
    obtaining a wellbore fluid sample from a wellbore fluid returning from an annulus of a wellbore;
    combining the wellbore fluid sample with a diluent to form a diluted wellbore fluid sample;
    analyzing the diluted wellbore fluid sample to determine one or more fluid properties;
    separating at least a portion of the diluent from the wellbore fluid sample in the diluted wellbore fluid sample; and
    recycling the separated portion of the diluent for re-use,
    wherein the step of recycling comprises compressing the separated portion of the diluent and recovering heat generated by the step of compressing for evaporation of the portion of the diluent from the wellbore fluid sample.

18. A method according to 17 further comprising condensing the separated vapor at a temperature of from about −40° F. to about 110° F. to form a condensed diluent.

19. A method according to claim 18, further comprising filtering the condensed diluent.

* * * * *